US010111905B2

(12) United States Patent
Weisshaar et al.

(10) Patent No.: US 10,111,905 B2
(45) Date of Patent: Oct. 30, 2018

(54) ANTIBACTERIAL PHARMACEUTICAL PREPARATION

(71) Applicant: ORTHOGEN AG, Düsseldorf (DE)

(72) Inventors: Maria-Paz Weisshaar, Bonn (DE); Julio Reinecke, Köln (DE); Peter Wehling, Düsseldorf (DE)

(73) Assignee: ORTHOGEN AG, Düsseldorf (DE)

( * ) Notice: Subject to any disclaimer, the term of this patent is extended or adjusted under 35 U.S.C. 154(b) by 0 days.

(21) Appl. No.: 14/038,358

(22) Filed: Sep. 26, 2013

(65) Prior Publication Data

US 2014/0093545 A1   Apr. 3, 2014

(30) Foreign Application Priority Data

Sep. 28, 2012   (DE) .......................... 10 2012 019 088

(51) Int. Cl.
   *A61K 35/14*   (2015.01)
   *A61K 45/06*   (2006.01)

(52) U.S. Cl.
   CPC .............. *A61K 35/14* (2013.01); *A61K 45/06* (2013.01); *Y02A 50/402* (2018.01); *Y02A 50/475* (2018.01); *Y02A 50/478* (2018.01); *Y02A 50/481* (2018.01)

(58) Field of Classification Search
   None
   See application file for complete search history.

(56) References Cited

U.S. PATENT DOCUMENTS

| 2008/0286379 A1 | 11/2008 | Reinecke |
| 2009/0047242 A1 | 2/2009 | Reinecke et al. |
| 2009/0304677 A1* | 12/2009 | Ichim ................. A61M 1/3679 424/130.1 |
| 2010/0267622 A1* | 10/2010 | Jiang .................. A61K 39/0008 514/2.4 |
| 2012/0237525 A1 | 9/2012 | Wehling et al. |
| 2012/0237587 A1 | 9/2012 | Wehling |
| 2013/0209528 A1* | 8/2013 | Levi et al. ..................... 424/400 |

FOREIGN PATENT DOCUMENTS

| EP | 1 984 006 | 8/2007 |
| EP | 2 156 841 | 2/2010 |
| WO | WO2006/007529 | 1/2006 |
| WO | WO 2010118979 A1 * | 10/2010 | ............. A61K 35/12 |
| WO | WO2011/082 950 | 7/2011 |

OTHER PUBLICATIONS

Vlassov, A.V. et al. 2012. [available online Apr. 1, 2012]. Exosomes: current knowledge of their composition, biological functions, and diagnostic and therapeutic potentials. Biochimica et Biophysica Acta 1820: 940-948. specif. pp. 940, 941.*
Smith, J.W. et al. 1995. Infectious arthritis. Clinical Infectious Diseases 20(2): 225-230. specif. pp. 225-227.*
Alpar, H.O. et al. Types of immune defense mechanisms. In: Pharmaceutical Biotechnology. CRC Press (publisher).Second edition. Copyright 2006.Taylor & Francis Group, LLC. Ed.: Michael J. Groves.Boca Raton, FL.p. 320.*
Caby, M.-P. et al. 2005. Exosomal-like vesicles are present in human blood plasma. International Immunology 17(7): 879-887. specif. pp. 879-880.*
Thery, C. et al. Isolation and characterization of exosomes from cell culture supernatants and biological fluids. In: Current Protocols in Cell Biology. Copyright 2006. John Wiley & Sons, Inc. Wiley Online Library, pp. 3.22.1-3.22.29. specif. pp. 3.22.1, 3.22.2, 3.22. 12.*
Bhatnagar, S. et al. Nov. 1, 2007. Exosomes released from macrophages infected with intracellular pathogens stimulate a proinflammatory response in vitro and in vivo. Blood 110(9): 3234-3244. specif. p. 3234.*
Hirsch, J.G. Jul. 1, 1980. Comparative bactericidal activities of blood serum and plasma serum. Journal of Experimental Medicine 112(1): 15-22. specif. pp. 15, 16, 17, 18, 19.*
Giri, P.K. et al. 2008. Exosomes derived from M. bovis BCG infected macrophages activate antigen-specific CD4+ and CD8+ T cells in vitro and in vivo. PLoS One 3(6): 1-10. specif. pp. 1, 2.*
Verreck, F.A.W. et al. 2006. Phenotypic and functional profiling of human proinflammatory type-1 and anti-inflammatory type-2 macrophages in response to microbial antigens and IFN-gamma and CD40L-mediated costimulation. Journal of Leukocyte Biology 79: 285-293. specif. pp. 285, 292.*
Giamarellos-Bourboulis, E.J. et al. 2012.The immune response to severe bacterial infections: consequences for therapy. Expert Reviews in Anti-Infective Therapy 10(3): 369-380. specif. p. 369.*
Lorincz, A et al.: Neutrophilic granulocytes produce different microvesicles upon stimulation with different agents (Abstract), in: J. of Extracellular Vesicles 2012, vol. 1 Supplements, Scientific Program 2012 ISEV meeting Wednesday Apr. 18.
Timar, Cs. et al.: Neutrophilic granulocyte-derived microvesicles in vitro and in vivo (Abstract), in: J. of Extracellular Vesicles 2012, vol. 1 Supplements, Scientific Program 2012 ISEV meeting Wednesday Apr. 18.
Weisshaar, M.-P. et al: Autologous conditioned cell-free serum (ACS) contains exosomes showing anti-inflammatory activity. (Abstract), in: J. of Extracellular Vesicles 2012, vol. 1 Supplements, Scientific Program 2012 ISEV meeting Wednesday Apr. 18.
Rachmachandra, L. et al.: *Mycobacterium tuberculosis* synergizes with ATP to induce release of microvesicles and . . . in: Infection and Immunity, Dec. 2010, p. 5116-5125.
Colino, J., Snapper C.M.: Dendritic cell-derived exosomes express a *Streptococcus pneumoniae* capsular polysaccharide type 14 . . . in: Infection and Immunity, vol. 75, No. 1, 2007, p. 220-23.

* cited by examiner

*Primary Examiner* — Renee Claytor
*Assistant Examiner* — Sharon M Papciak
(74) *Attorney, Agent, or Firm* — Ursula B. Day, Esquire

(57) ABSTRACT

The present invention refers to a pharmaceutical preparation for use as an antibacterial agent, where the pharmaceutical preparation is prepared by a method comprising the steps of bringing a full blood sample taken from a patient in contact with a vessel or container and incubating the sample.

11 Claims, 2 Drawing Sheets

ANTIBACTERIAL PHARMACEUTICAL PREPARATION

CROSS-REFERENCES TO RELATED APPLICATIONS

This application claims the priority of German Patent Application Serial No. 10 2012 019 088.3, filed Sep. 28, 2012 pursuant to 35 U.S.C. 119(a)-(d), the subject matter of which is incorporated herein by reference.

BACKGROUND OF THE INVENTION

The present invention relates to an antibacterial agent, in particular an antibacterial pharmaceutical preparation.

The human body is colonized by large amount of bacteria. For example, bacteria are found in the intestines, on the skin and in the mouth cavity. In their environment, humans are exposed to countless bacteria that are also taken up through respiration or through nutrition.

Besides important functions those bacteria fulfill on or in the human body, they can also be agents of disease, for example when infections occur in wounds or organs or sepsis is triggered. Aside from the skin, the mucous membranes of the respiratory system or those of the digestive tract are often afflicted.

When certain barrier functions in the body are compromised, bacteria can invade the human body, however, even with fully functioning barriers, bacteria can invade, for example, the skin or the mucous membranes, wherein the bacteria use specialized mechanisms. When the natural immunity of the body is weakened, even normal bacterial flora of the exterior and interior surfaces of the body can lead to opportunistic diseases, even if the respective bacteria normally are non-pathogenic.

Many bacterial infections turn out to be harmless. But depending on the specific germ, the locality of the infection and the immunity status of the patient, bacterial infections can also lead to severe diseases.

Nowadays, bacterial infections are normally fought through the administration of antibiotics to a patient. A growing problem when administering antibiotics is represented by the growing number of resistant strains of bacteria. Many antibiotics are no longer effective against certain bacteria. Multi-resistant germs or bacteria are a particular medical problem, where the bacteria have become resistant against several types of antibiotics and resistances are transferred from bacterium to bacterium.

The problem with administering antibiotics is that not only pathogenic bacteria are killed by the antibiotic but also those bacteria that are desirable and useful for the human body. If the intestinal flora has been destroyed due to the treatment with an antibiotic, then it does not simply represent an inconvenience. In such a case, even a bacterium, which normally exists in the healthy intestinal flora and due to competitive inhibition remains at low count in the intestine, if having become resistant to antibiotics, for example *Clostridium*, can multiply unobstructed and can trigger diseases.

The administration of antibiotics can also be complicated through incompatibilities and/or allergies. A frequent case is penicillin allergy. Allergic reactions range from reddening of the skin to anaphylactic shock.

It would therefore be desirable to provide an alternative antibacterial preparation, which preferably obviates one or more of the prior art shortcomings and to avoid the drawbacks of the use of antibiotics as afore-discussed.

The present invention resolves prior art problems by providing an antibacterial agent in the form a pharmaceutical preparation that does not require the use of antibiotics.

Advantageously, such a preparation is fast and easy to produce and is cost effective. Also such a preparation should have a good body compatibility.

SUMMARY OF THE INVENTION

According to one aspect of the present invention, a pharmaceutical preparation is provided that has desired antibacterial properties. The pharmaceutical preparation is administered to a patient in need of treatment for a bacterial infection. The pharmaceutical preparation is produced by a method including the steps of contacting a whole blood sample collected from a patient with a vessel or container and incubating the whole blood sample. Before the step of contacting the whole blood sample with the vessel or container, the method preferably additionally includes the step of collecting said whole blood sample from said patient.

The present invention may also be described as a method of treating a bacterial infection in a patient in need thereof, comprising the following steps: providing a whole blood sample and a vessel or container, contacting said whole blood sample with said vessel or container, incubating said whole blood sample contacted with said vessel or container, which results in a pharmaceutical preparation being produced and administering an effective amount of the pharmaceutical preparation produced in the previous step to said patient. Preferably, said method of treating a bacterial infection, before the step of providing said whole blood sample, additionally includes the step of collecting said whole blood sample, preferably from said patient.

The incubation produces a conditioned whole blood sample. The conditioned whole blood sample produced by the incubation has an antibacterial effect. When separating certain cell constituents, a conditioned plasma is obtained from which after blood coagulation a conditioned serum is obtained.

It is known that conditioned human whole blood contains exosomes. Exosomes are small vesicles, which are secreted from the cells into their environment. Exosomes are for example contained in such biological liquids as serum, urine and synovial liquids. Most types of cells are able to secrete exosomes. The secretion results through release from the cell's plasma membrane. Depending on the cell type in which they are generated, exosomes contain among others a variable combination of proteins.

WO 2006/007529 A2 describes exosomes in conditioned human whole blood as well as their therapeutic application, in particular in example 14. It generally describes as areas of application the inhibition of immune reactions and by way of example, lumbar radicular pains, rheumatoid arthritis, juvenile Morbus Still, aka systemic juvenile idiopathic arthritis, hay fever and grass and pollen allergies.

It was surprisingly found that an antibacterial effect in the pharmaceutical preparation results from the incubation of a whole blood sample which finding serves as a basis for the pharmaceutical preparation of present invention.

In order to obtain the pharmaceutical preparation having an antibacterial effect by incubation of a whole blood sample in a vessel or container it is unnecessary to add any external stimulators or activators of antibacterial activity, and preferably no toxic external stimulators or activators of antibacterial activity are added. It is possible not to add any external stimulators or activators of antibacterial activity at all.

The antibacterial effect of the pharmaceutical preparation can be determined in a simple manner, for example with an inhibitory zone test (Hemmhoftest) with which the sensitivity of bacteria against antibacterial an active substance can be tested. In that test, the growth of a bacterial layer on an agar plate is tested by placing little pieces of filter leaflets that were saturated with an effective antibacterial agent on the agar plate. Since the antibacterial agent diffuses into the agar, no growth of bacterial layer occurs around the filter leaflets.

Another way of determining the antibacterial effect of the agent is with a culture inhibitor.

Similarly, an amount of the pharmaceutical preparation effective for treatment may be determined e.g. by an agar diffusion test or a test for growth inhibition in liquid cultures, as described in Examples 3 and 4 and using appropriate bacterial cultures. An effective amount may also be determined e.g. by using animal models, such as mice or rats, or by other means of determining an effective amount of an antibacterial agent known to a person skilled in the art.

Due to its antibacterial effect such pharmaceutical preparation is useful for therapeutic purposes including a prophylactic purpose in a disease or an affliction caused by bacteria, in particular infectious diseases. The pharmaceutical preparation can be administered by itself or in combination with other effective agents. In this manner, the pharmaceutical preparation constitutes an alternative to the use of antibiotics.

The pharmaceutical preparation of the present invention may afford, for example, a simple, cost effective and/or rapid production. By carrying out a series of easy steps in the production and without the need for special or complicated equipment and materials, in a minimum of steps and a few hours, a ready-to-use pharmaceutical preparation is realized without having to add any substances foreign to the body during production or such other substances which will have to separated again later in the production. By using exclusively a body's own substances, in this manner, an especially compatible antibacterial agent can be realized. The pharmaceutical preparation of the present invention offers in addition the possibility to avoid or eliminate the afore-stated drawbacks that are present with an antibiotic, e.g. in that resistances may be avoided and side effects may be eliminated or reduced.

The pharmaceutical preparation of the present invention contains preferably exosomes and an especially preferred pharmaceutical preparation contains exosomes that are generated during the incubation of the whole blood sample in the vessel or container. It is one of the findings of the present invention that a pharmaceutical preparation containing exosomes is especially efficacious.

Hereinafter, where embodiments of the present invention are described using the term "containing" or "comprising" certain subject matter, e.g. methods steps or constituents, it is understood that preferred embodiments consist of said subject matter, except where the context dictates otherwise.

The average diameter of the exosomes in the pharmaceutical preparation containing the exosomes of the present invention, as established by means of a transmission electron microscope, is preferably between 30 and 200 nm, in particular between 50 and 190 nm, between 70 and 180 nm, between 90 and 160 nm or between 100 and 150 nm. Exosomes of this size are the basis for an especially high efficacy, while larger vesicles represent essentially damaged exosomes and aggregates.

The method for producing the pharmaceutical preparation containing the exosomes of the present invention includes preferably a step of concentrating the exosomes after the sample has been incubated in order to further increase the antibacterial efficacy.

The concentration of the exosomes for example can be realized through centrifugation at 100,000 g, as such strong accelerations are especially suitable to concentrate exosomes. Such centrifugation is preferably conducted at 30 min., especially at least 60 min., which renders the exosomes especially effective. The pellet formed by the centrifugation then contains the exosomes. The pellet can then be taken up in a liquid and optionally filtrated, for example through a 0.2 µm filter.

The pharmaceutical preparation preferably contains serum or plasma. The presence of serum and plasma in addition to the exosomes increases the antibacterial efficacy of the pharmaceutical preparation. While these constituents of the pharmaceutical preparation, the serum or plasma and the exosomes, each by themselves have antibacterial efficacy, a combination of these constituents has a particularly high efficacy.

The preferred pharmaceutical preparation of the present invention thus contains a combination of serum, plasma and exosomes. An especially preferred pharmaceutical preparation of the present invention contains a combination of serum and plasma and exosomes as they are generated during incubation.

Alternatively, the pharmaceutical preparation of the present invention can comprise just exosomes but no serum or plasma, and in particular may consist of exosomes. It has been found in connection with the present invention that the antibacterial effect of the exosomes is independent of the presence of either serum or plasma or both of these constituents.

According to a further alternative, the pharmaceutical preparation of the present invention can also comprise just plasma and serum but no exosomes, and in particular may consist of serum or plasma.

According to a less preferred alternative, the method for producing the pharmaceutical preparation of the present invention comprises the separation of exosomes present or the serum or the plasma after the incubation. For example, exosomes can be isolated by means of differential ultracentrifuging, saccharose gradient and/or saccharose cushion.

Optionally, an exosomes containing pharmaceutical preparation of the present invention, in particular one that consists of exosomes can be so modified that the exosomes are submitted to lysis, for example to hypotone lysis by means of dissolving the exosomes in water. The lysis results in the exosomes releasing their content.

The serum or plasma contained in the pharmaceutical preparation according to the present invention preferably contains cytokines- and/or growth factors. Preferably, the pharmaceutical preparation does not comprise a corticosteroid.

According to a preferred embodiment the method for production of the pharmaceutical preparation of the present invention comprises the following step: removing the cellular constituents of the whole blood sample after the incubation and before administering the pharmaceutical composition. For such a separation it is suitable to carry out a centrifugation, for example, a short centrifugation at low revolutions, about 10 minutes at 1000 g or a filtration.

Incubation of the whole blood sample is preferably carried out for a period of up to 72 hours, in particular a time period of 1-48 hrs, 2-24 hrs, 3-12 hrs, 4-10 hrs, 5-8 hrs or 6 hrs. It has been shown that the best antibacterial efficacy is realized with an incubation period of about 6 hrs. The conditioned preparations so formed and realized at such incubation time retain the maximal amount of exosomes that are intact. Upon longer incaution periods, the portions of aggregates and damaged exosomes increases and at shorter incubation periods, the amount of exosomes is not yet optimal.

The incubation is preferably carried out at a temperature of 0° C. to 45° C., preferred at temperatures of 10° C. to 43° C., 20° C. to 41° C., 30° C. to 40° C., 35° C. to 39° C., 36° C. to 38° C. or 37° C. At those temperatures, the formation of antibacterial activity is particularly effective in the pharmaceutical preparation of the present invention. That means especially that an increased generation of exosomes can be regularly observed.

Suitable vessels or containers for carrying out the method for producing the pharmaceutical preparation of the present invention are for example hypodermic needles, tubes such as vacuum tubes, micro titer plates and transfusion bags. The vessel or container preferably comprises a surface for contact with the whole blood sample, the surface that can comprise or be glass, plastic, corundum or quartz or a combination of these. A preferred plastic is selected from the group consisting of polystyrene, polyvinyl chloride, polycarbonate, polyethylene and polypropylene.

According to a preferred embodiment the vessel or container includes macroscopic particles and the whole blood sample is in contact with the macroscopic particles during incubation. Macroscopic particles here are understood to be particles that are visible when viewed with the naked eye. The macroscopic particles serve the purpose to enlarge the surface of contact with the whole blood sample and can be in the shape of spheres, granulates, powder, gels or wool. Preferred materials are glass, plastic, corundum and or quartz. Especially preferred are glass spheres. The surface of the macroscopic particles can optionally be modified, for example by incubation with a caustic agent such as 50% v/v $CrSO_4$ with subsequent repeated rinsing. When using the afore-stated vessels or containers and/or the named macroscopic particles an improved conditioning and a reinforcement of the antibacterial properties of the pharmaceutical preparation is realized.

With respect to obtaining a conditioned whole blood containing exosomes, plasma or serum reference is made to WO 2006/007529 A2, in particular to example 14 thereof.

Conditioned serum is also known under the name Orthokine®. In a preferred embodiment of the present invention Orthokine® is utilized as a pharmaceutical preparation of the present invention.

The pharmaceutical preparation of the present invention is preferably administered to the patient from whom the whole blood sample has been taken. Thus, the sample is preferably an autologous pharmaceutical preparation and not an allogeneic pharmaceutical preparation, especially for reasons of safety.

The pharmaceutical preparation can be administered as a local or a systemic administration. Among others, this is determined by the accessibility of the affected body part or organ and by the type and localization of the bacteria that are to be fought by the antibacterial property of the pharmaceutical preparation.

Suitable ways of administration are parenteral, in particular intravenous, intra-arterial, intramuscular, intra-articular, epi/peridural, subcutaneous or intra-peritoneal, topical, pulmonal, nasal, rectal, dermal, conjuctival or otic.

The pharmaceutical preparation of the invention can be applied in therapies of local or systemic diseases. Preferably, the pharmaceutical preparation is used for therapy of a disease which is caused by or based on one or more of the following bacteria: *Bordetella, Borellia, Brucella, Campylobacter, Chlamydia, Clostridium, Corynebacteria, Enterobacteria, Enterococcus, Escherichia, Francisella, Haemophilus influenzae, Helicobacter, Klebsiella, Legionella, Leprospira, Listeria, Mycobacteria, Mycoplasma, Neisseria, Proteus, Pseudomonas, Rickettsia, Salmonella, Shigella, Staphylococcus, Streptococcus, Treponema pallidum, Ureaplasma, Vibrionaceae* and *Yersinia*.

Diseases are: infections such as septic infections, bone infections, bacterial meningitis, joint infections (optionally other than bacterial arthritis), skin infections, infections of wounds, such a post-operative wound infections or infection of burn wounds; infection in the mouth area, genital infections, sexually transmitted diseases, urinary tract infections and eye infections, abscesses, phlegmon, mastitis, tonsillitis, sinusitis, otitis media, dermatitis, upper respiratory tract infections, pneumonia, salmonellose, gastritis, food poisoning or diarrhea.

The pharmaceutical preparation is optionally provided for use in a combination therapy with a further antibacterial agent, which is administered at the same time or at some time earlier or later in the same or in different preparations. For the purpose of combination therapy known antibacterial agents such as antibiotics are suitable.

A preferred antibiotic for use in a combination therapy is selected from the group consisting of aminoglycoside, β-lactame, chinolone, glycopeptide, polyketide, polypeptidantibiotics and sulfonamides. The antibiotic is administered in a manner known by those skilled in the art.

Patients can be either humans or animals that suffer from a bacterial infection or generally a disease or condition caused by bacteria and which can be treated therefor, or in which such infection, disease or condition is to be prevented. Thus, the pharmaceutical preparation of the present invention can be produced for therapy of a human or an animal, such as for example, dogs, cats, horses, cows, pigs, goats or camels.

BRIEF DESCRIPTION OF THE DRAWINGS

Other features and advantages of the present invention will be more readily apparent upon reading the following description of currently preferred exemplified embodiments of the invention with reference to the accompanying drawing, in which:

FIG. 1A shows the growth curve of a test culture which was treated with a pharmaceutical preparation of the present invention which during production was incubated for 6 hrs (rhombic symbols) and next to it is the corresponding comparative culture without the pharmaceutical preparation (square symbols). The X-axis shows the time of culture growth in minutes and the Y-axis shows the optical density at 560 nm.

FIG. 1B corresponds to FIG. 1A except during production, the pharmaceutical preparation was incubated for 24 hrs.

DETAILED DESCRIPTION OF PREFERRED EMBODIMENTS

Figure 1:
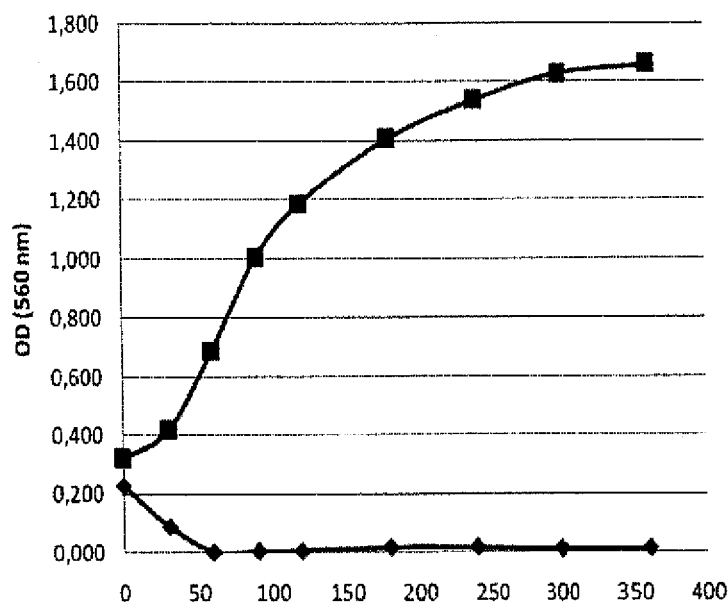
FIG. 1 shows the result of experiments with liquid cultures of *E. coli* K12 showing growth inhibition by the pharmaceutical preparation of the present invention.
Figure 1:
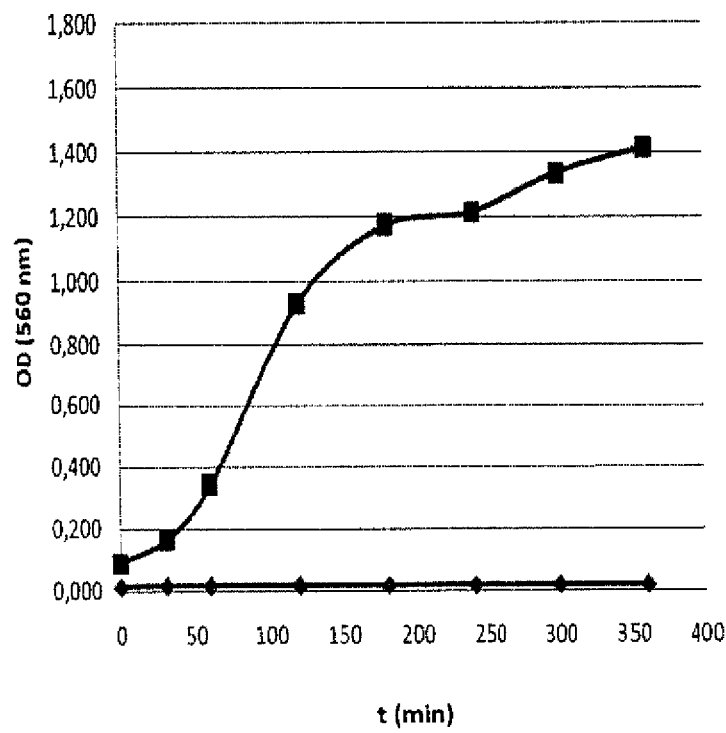

Example 1: Production of the Pharmaceutical Preparation of the Present Invention From healthy test subjects in each case 50 ml whole blood were collected with a 60 ml syringe (Orthogen). The syringes each contained about 200 glass spheres with a diameter of 3.5 mm which provided total surface of 7700 mm². The spheres had been washed with distilled water until the pH value of the water, after the rinse, was identical to the one before rinsing such that the conductivity of the water did not change anymore.

Immediately after the blood was drawn, the blood was incubated at 37° C. in each of the aseptically sealed syringes. The incubation times in different measurement clusters were 3 hrs, 6 hrs, 12 hrs or 24 hrs.

Example 2: Analysis of Exosomes 2.1 Isolation of Exosomes

The exosomes were isolated by standard procedures by means of ultracentrifugation, saccharose gradient and/or saccharose cushion (40% saccharose). The exosome pellets were taken up in 200 µl PBS buffer. In some of the cases, the exosomes were taken up in water.

2.2 Transmission Electron Microscopy

The exosomes were visualized by means of transmission electron microscopy utilizing a copper grid and dying the sample with uranylacetate and quantified through measurements with NanoSight (NTA) from NanoSight Ltd. Wilshire, UK. It was shown that the greatest number of intact exosomes ($2.89 \times 10^8$), having an average diameter of 100-150 nm was present after an incubation period of 6 hrs.

The 24 hrs incubation resulted likewise in a great number of Exosomes with an average diameter of 180 nm. This might point to the fact that a certain portion may have constituted aggregates and damaged exosomes.

2.3 Analysis of Protein Content

The protein content was determined through SDS-polyacrylamide gradient gels and Western Blot utilizing anti-CD63-antibodies. It is known that CD63 is a marker for exosomes.

From the strength of the CD63 band in samples of different incubation periods, the Western Blot showed that during the incubation time there was active generation of new exosomes.

Example 3: Agar Diffusion Test: Inhibitory Zone Test

The antibacterial effect of the pharmaceutical preparation of the present invention were tested at incubation times 3, 6, 12, or 24 hrs with an agar diffusion test, the Todd-Hewitt-Agar test.

Isolated exosomes taken up in buffer (without the serum or plasma) and the corresponding supernatant of the separation (without the exosomes) were each tested separately.

Round filter leaflets were saturated with 10, 20 and 30 µl of each of the solutions and placed on corresponding sectors of an agar plate.

The filter leaflets that were saturated with the supernatant showed with samples of all incubation times inhibitory zones of a size commensurate with the amount of supernatant used. The leaflets that were saturated with the exosomes samples showed inhibitory zones as well that were likewise dependent on the amount of sample used. The largest inhibitory zone was from the sample of the 6 hrs incubation period. This shows that the greatest number of intact and active exosomes is realized after 6 hrs of incubation of the whole blood sample. Exosomes and supernatant of the other incubation periods are however also useful.

Also tested were pharmaceutical preparations according to the present invention that contained both serum and exosomes, which elicited the largest inhibitory zones.

Example 4: Growth Inhibition in Liquid Cultures

In examining a bacteriostatic or bactericidal effect of the pharmaceutical preparation, liquid cultures of *Salmonella* 1535 and *Escherichia coli* K12 were utilized. Pharmaceutical preparations that had been incubated for 6 hrs, respectively 24 hrs and that contained serum as well as exosomes were added to the test cultures. To a control culture a control solution was added that was prepared the same way as the pharmaceutical preparation except that no incubation was carried out. Each of the comparison cultures used was cultivated without any additions.

Each of the cultures was cultivated according to standard methods. After adding the pharmaceutical preparation, respectively the control solution, growth of the test cultures and the control culture, respectively, were observed over a six-hour observation time through measurement of the optical density, as well as the growth of the comparison cultures.

Figure 2:
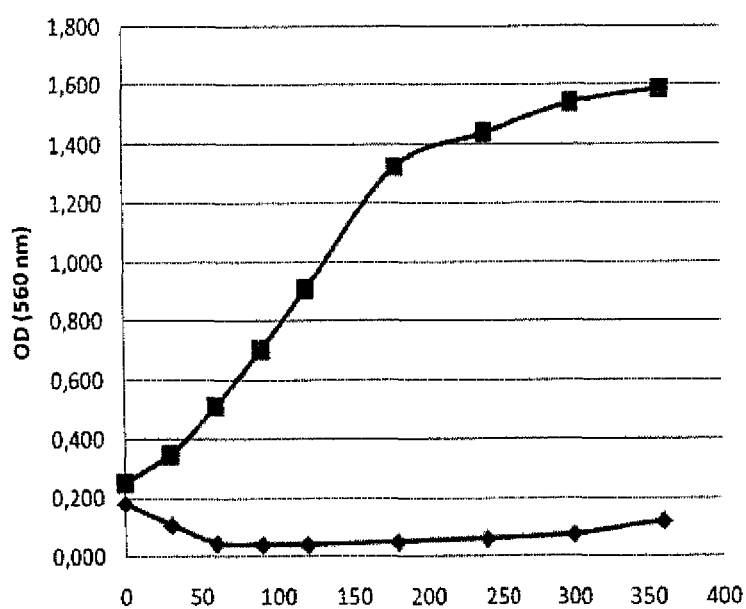
FIG. 2 shows the result of experiments as in FIG. 1 except that for the liquid culture, *salmonella* 1535 was used.
Figure 2:
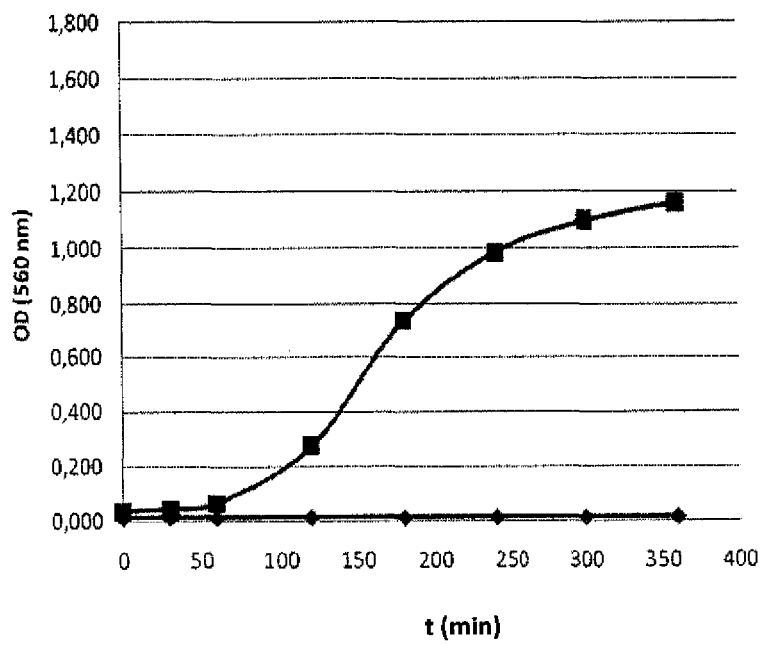

Results are shown in FIGS. 1 and 2. While the comparison cultures had grown during the observation period to almost saturation, the optical density in the test cultures remained in the range of the starting values or was slightly lower. The control culture grew during the observation period to the same saturation density as the corresponding comparison culture. This shows that the incubation indeed generates the antibacterial activity of the pharmaceutical preparation of the present invention.

While the invention has been illustrated and described as above, it is not intended to be limited to the details shown since various modifications and changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents:

1. A method of treating a bacterial infection in a patient in need thereof, comprising the following steps:
   contacting a whole blood sample with a vessel or container, wherein the vessel or container contains macroscopic particles from glass, plastic, corundum and or quartz and wherein during incubation the whole blood sample is in contact with the macroscopic particles;
   incubating said whole blood sample in contact with said vessel or container, which results in an antibacterial agent in the form of a pharmaceutical preparation being produced, wherein the pharmaceutical preparation comprises exosomes that have been generated during the period of said incubation;
   and
   administering an effective amount of the pharmaceutical preparation to said patient who is in need of for treatment for bacterial infection, thereby treating the bacterial infection, wherein the exosomes of the pharmaceutical preparation interact with the bacteria to inhibit bacterial growth; said bacterial infection is caused by one or more bacteria selected from *Salmonella*.

2. The method of claim 1, wherein an average diameter of the exosomes as determined by transmission electron microscopy is in the range between 30 and 200 nm.

3. The method of claim 1, wherein the pharmaceutical preparation comprises serum or plasma.

4. The method of claim 1, further comprising the step of removing the cellular constituents of the whole blood sample after said incubation and before said administration.

5. The method of claim 1, wherein said incubation is carried out during a time period of up to 72 hours.

6. The method of claim 1, wherein said incubation is carried out at a temperature from 0° C. to 45° C.

7. The method of claim 1, wherein the vessel or container includes a surface for contacting the whole blood sample that comprises glass, plastic, corundum or quartz or a combination thereof.

8. The method of claim 7, wherein the plastic is selected from the group consisting of polystyrene, polycarbonate, polyethylene, and polypropylene.

9. The method of claim 1, wherein said whole blood sample is from said patient.

10. The method of claim 1, wherein said administration is a local or systemic administration.

11. The method of claim 1, further comprising administering a further antibacterial agent to said patient.

* * * * *